United States Patent [19]

Harris

[11] 4,223,673
[45] Sep. 23, 1980

[54] DEVICE FOR PUCKERING THE FLESH TO ASSIST IN INJECTIONS

[76] Inventor: William J. Harris, 129 Hampshire Rd., Wellesley Hills, Mass. 02181

[21] Appl. No.: 950,479

[22] Filed: Oct. 11, 1978

[51] Int. Cl.³ .............................................. A61M 5/00
[52] U.S. Cl. .................................... 128/215; 128/321; 128/327; 128/346; 294/31.2
[58] Field of Search ............. 24/257, 262; 128/214 R, 128/215, 325–327, 321–324, 346, 352, 361; 294/31.2

[56] References Cited

U.S. PATENT DOCUMENTS

| | | | |
|---|---|---|---|
| 1,953,074 | 4/1934 | Cohen | 128/327 |
| 2,447,474 | 8/1948 | Hammond | 128/303 A |
| 2,584,397 | 2/1952 | Pitman | 128/215 X |
| 2,704,071 | 3/1955 | Becker | 128/215 |
| 3,620,209 | 11/1971 | Kravitz | 128/215 X |
| 3,760,803 | 9/1973 | Boothby | 128/215 |
| 3,802,437 | 4/1974 | Kees | 128/325 |

FOREIGN PATENT DOCUMENTS 219012  7/1909  Fed. Rep. of Germany ........... 128/327

Primary Examiner—Dalton L. Truluck
Attorney, Agent, or Firm—Weingarten, Maxham & Schurgin

[57] ABSTRACT

A pair of parallel clamping arms hold an adjustable loop, which when applied to the limb, provides a device for puckering the flesh for injections. The parallel clamping arms extend from a pair of bent arms which have a spring attached thereto at the lower portion thereof. The spring serves to push the clamping arms inwardly and to maintain the clamping arms in a normally pressed together condition. The adjustable loop is formed of two cooperating interlocking strips which overlap one another. The loop is adjustable by varying the degree of overlap of the two strips.

4 Claims, 3 Drawing Figures

DEVICE FOR PUCKERING THE FLESH TO ASSIST IN INJECTIONS

BACKGROUND OF INVENTION

This invention relates to a device to assist diabetics in injecting insulin.

A person who is diabetic and who is required to take insulin usually must take at least one injection a day, and in some cases twice a day. Inasmuch as a point of injection cannot be utilized again until it heals, diabetics have a continuous problem of finding and utilizing suitable areas in the body for injections.

In some parts of the body, as for example, the arm, it is necessary for the diabetic to pinch or pucker a portion of the flesh on the arm in order to be able to make a proper injection.

One of the objects of this invention is to provide a device which will enable a diabetic to make the proper pinch on his arm so that he can make a proper injection of insulin.

Other objects and advantages of this invention will be apparent from the description and claims which follow taken together with the appended drawings.

SUMMARY OF INVENTION

The invention comprises generally a clamping device. The device has a gripping portion, a clamping means having a pair of parallel clamping arms and being attached to the gripping portion, a flexible loop adjustable in length and attached to the clamping arms, and spring means tending to push the arms inwardly.

The loop is preferably made of a flexible material, such as cloth, fabric or thin plastic. The loop has two separable portions which can be adjusted to the size of the limb, and thus can be used with children as well as adults. Various means for adjusting the length of the loop can be used including Velcro nylon loops, snap fasteners, hooks and eyes, etc.

SPECIFIC EXAMPLE OF INVENTION

Figure 1:
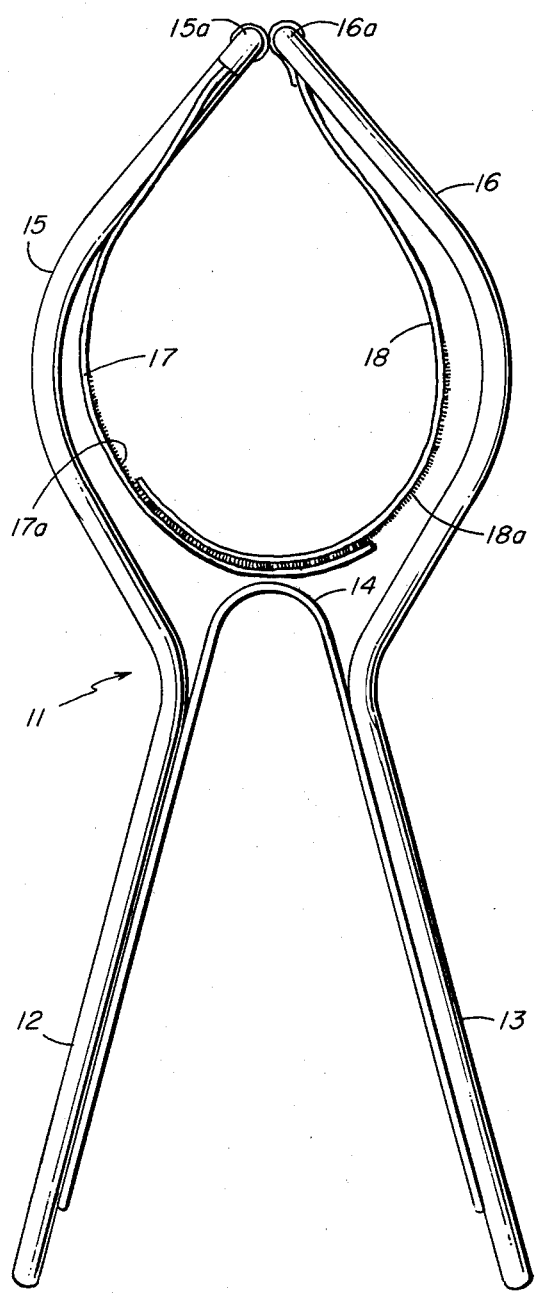
FIG. 1 is a plan view of one embodiment of this invention.
Figure 2:
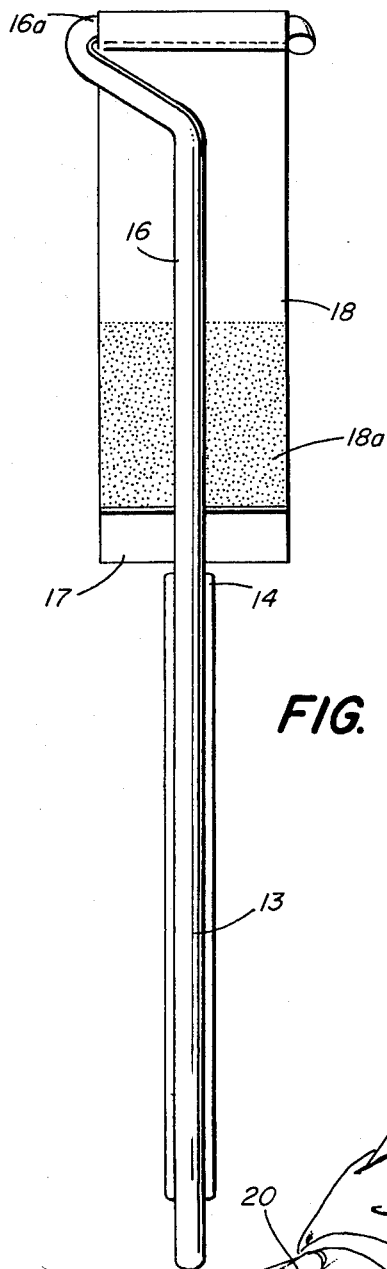
FIG. 2 is a side view.

Referring now to the drawings, there is illustrated therein an embodiment 11 of this invention which comprises a pair of bent arms 15 and 16 attached to a spring 14 at their lower portions 12 and 13 and having clamping, parallel end portions 15a and 16a which are normally kept pressed together by the action of the spring 14. Attached to the clamping portions 15a and 16a are two cooperating, flexible strips 17 and 18 which, when attached to one another, form a loop. Strips 17 and 18 have loops formed at one end thereof through which extend respective end portions 15a and 16a.

Figure 3:
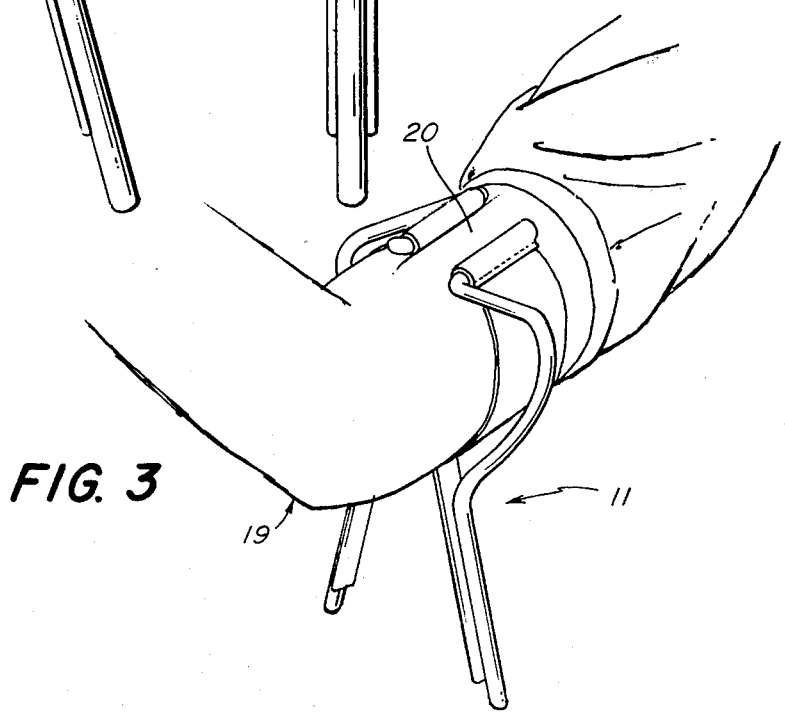
FIG. 3 is a perspective view of the invention as applied to the arm of a person.

When the devide 11 is placed on a portion of the arm above the elbow 19, as illustrated in FIG. 3, the pressure of the loop causes the flesh to form a puckering portion 20 into which the insulin needle can be inserted.

The loop is illustrated in the drawings by portions 17 and 18 which have interlocking nylon loop surfaces 17a and 18a, as for example, Velcro, and are thus adjustable to the size of the portion of the arm being used.

Other adjustable means which can be used to achieve adjustability include fasteners such as snap fasteners, stud fasteners or hook and eye fasteners.

I claim:

1. A device for puckering the flesh on a limb of a person to assist in injections, comprising a gripping portion; clamping means attached to said gripping portion and having a pair of parallel clamping arms; a flexible loop formed of a pair of overlapping, interlocking strips, said loop being adjustable in length by means of adjusting means which vary the amount of overlap of said pair of strips at a bottom portion thereof facing said gripping portion, each of said strips having one end attached to one of said clamping arms; and spring means attached to said gripping portion and tending to push said arms in an inward direction.

2. The device of claim 1 wherein said gripping and clamping portions comprise a pair of bent rods, each having a clamping arm, an outwardly flaring arcuate portion essentially perpendicular to said clamping arm, and an outwardly flaring gripping portion in the same plane as said arcuate portion.

3. The device of claim 1 wherein said pair of clamping arms extends from said clamping means in a direction transverse of said inward direction and wherein each of said strips has another loop formed around said one at said one end, said one of said clamping arms extending through said another loop.

4. The device of claim 1 wherein said adjusting means comprise interlocking nylon loop surfaces.

* * * * *